United States Patent
Zhou et al.

(10) Patent No.: US 10,028,480 B2
(45) Date of Patent: Jul. 24, 2018

(54) GANODERMA LUCIDUM STRAIN SUITABLE FOR LARGE-SCALE LIQUID FERMENTATION CULTURE, METHOD OF MUTATION BREEDING THE SAME, AND USE OF THE STRAIN

(71) Applicant: YUNNAN MINGSHIDA-SCIENCE-TECH CO., LTD., Kunming (CN)

(72) Inventors: Yingkui Zhou, Kunming (CN); Meng Zhou, Kunming (CN); Nuo Zhou, Kunming (CN)

(73) Assignee: Yunnan Mingshida-Science-Tech Co., Ltd., Kunming (CN)

( * ) Notice: Subject to any disclaimer, the term of this patent is extended or adjusted under 35 U.S.C. 154(b) by 201 days.

(21) Appl. No.: 15/057,441

(22) Filed: Mar. 1, 2016

(65) Prior Publication Data

US 2016/0270359 A1 Sep. 22, 2016

(30) Foreign Application Priority Data

Mar. 18, 2015 (CN) .......................... 2015 1 0116700

(51) Int. Cl.
| | |
|---|---|
| *A01H 1/06* | (2006.01) |
| *A01H 15/00* | (2006.01) |
| *C12N 1/14* | (2006.01) |
| *C12R 1/645* | (2006.01) |
| *A01H 1/02* | (2006.01) |
| *A23L 2/38* | (2006.01) |
| *A23L 2/52* | (2006.01) |
| *C12N 15/01* | (2006.01) |

(52) U.S. Cl.
CPC ............... *A01H 15/00* (2013.01); *A01H 1/02* (2013.01); *A01H 1/06* (2013.01); *A23L 2/382* (2013.01); *A23L 2/52* (2013.01); *C12N 1/14* (2013.01); *C12N 15/01* (2013.01); *C12R 1/645* (2013.01); *A23V 2002/00* (2013.01)

(58) Field of Classification Search
None
See application file for complete search history.

(56) References Cited

FOREIGN PATENT DOCUMENTS

| | | |
|---|---|---|
| CN | 1342752 | 4/2002 |
| CN | 1854288 | 11/2006 |
| CN | 102876581 | 1/2013 |
| CN | 103299823 | 9/2013 |
| CN | 103548556 | 2/2014 |
| CN | 204070058 | 1/2015 |
| WO | 2015018076 | 2/2015 |

OTHER PUBLICATIONS

Sathesh-Prabu et al 2011, Journal of Radiation Industry 5(4): 285-295.*
Ya-Jie Tang, et al., Scale-Up Study on the Fed-Batch Fermentation of *Ganoderma lucidum* for the Hyperproduction of Ganoderic Acid and Ganoderma Polysaccharides, Process Biochemistry, 2011, 404-408, 46 Elsevier Ltd.
Xuan-Wei Zhou, et al., Applied Modern Biotechnology for Cultivation of Ganoderma and Development of Their Products, Applied Microbiology & Biotechnology, 2012, 941-963, 93, Springer.
Baojing Yuan, et al., Optimization of Exopolysaccharides Production from a Novel Strain of *Ganoderma lucidum* CAU5501 in Submerged Culture, Brazilian Journal of Microbiology, 2012, 490-497, 1517-8382.
Yin-Ping Zhang, et al., High Preparation and Mutagenesis of Protoplast of *Ganoderma lucidum*, Journal of Anhui Agri. Sci., 2012, 12379-12381, 40(25), China, Abstract only.

* cited by examiner

*Primary Examiner* — David H Kruse
(74) *Attorney, Agent, or Firm* — Sand & Sebolt

(57) ABSTRACT

Disclosed is a *Ganoderma Lucidum* strain suitable for large-scale liquid fermentation, named as *Ganoderma Lucidum* G2, deposited with China General Microbiological Culture Collection Center under the accession number CGMCC No. 3982 on Jul. 20, 2010, and a method of mutation breeding the same and use of the strain. The *Ganoderma Lucidum* strain which belongs to Ganodermataceae, genus *Ganoderma*, species red *Ganoderma Lucidum* is obtained by artificial mutagenizing and breeding. The production of mycelia using the *Ganoderma Lucidum* strain G2 is 80~120 times higher as compared with the production of mycelia using wild-type naïve *Ganoderma Lucidum* strain. The mycelia produced using the *Ganoderma Lucidum* strain G2 have higher contents of main pharmaceutical ingredients. The *Ganoderma Lucidum* strain suitable for large-scale liquid fermentation can be used for manufacturing oral solution or beverage comprising *Ganoderma* mycelia or extracts of *Ganoderma* mycelia as main active ingredient.

12 Claims, No Drawings

GANODERMA LUCIDUM STRAIN SUITABLE FOR LARGE-SCALE LIQUID FERMENTATION CULTURE, METHOD OF MUTATION BREEDING THE SAME, AND USE OF THE STRAIN

FIELD OF THE INVENTION

The present application generally relates to the industry of edible fungus, and in particular, relates to a *Ganoderma Lucidum* strain suitable for large-scale liquid fermentation, a method of obtaining a *Ganoderma Lucidum* strain suitable for large-scale liquid fermentation by mutagenizing and breeding, and use of the strain.

BACKGROUND OF THE INVENTION

*Ganoderma* is recognized as a high-value herb in traditional Chinese medicine. As early as in the Donghan dynasty more than 2,000 year ago, *Ganoderma* is recorded in the "Sheng Nong's herbal classic" as a herb which is beneficial for improving general health, health of cardiac system, intelligence, spirit, health of bones, action ability and life span. *Ganoderma* is a supreme herb which refers to one having significant therapeutic effect with little side effect. Among tens of thousands of herbs, supreme herbs are very rare. During the last decades, study on *Ganoderma* mycelia becomes a hot topic worldwide.

*Ganoderma* mycelia contain cells in which the nutrients absorbed by *Ganoderma* accumulate. Ganoderma mycelia have rich *Ganoderma* polysaccharide, *Ganoderma* organic germanium, *Ganoderma* polypeptides, triterpenes, 16 species of amino acids of which seven are essential to human, proteins, steroid, mannitol, courmarin glycosides, alkaloids, organic acids (primarily fumaric acid), and trace elements comprising P, Fe, Ca, Mn, Zn, etc. *Ganoderma* mycelia have significant use in medical cares, e.g. anti-tumor therapy, improvement in liver health, immunity, sleep condition, and health of cardiovascular system, delaying ageing and treatment of neurasthenia. However, although wild *Ganoderma Lucidum* strain collected in nature can propagate, they have many defects in industrial production and cannot meet requirements of large-scale production of *Ganoderma* products.

SUMMARY OF THE INVENTION

The present application aims to address some issues in the prior art, and provides a *Ganoderma Lucidum* strain suitable for large-scale liquid fermentation, a method of obtaining a *Ganoderma Lucidum* strain suitable for large-scale liquid fermentation by mutagenizing and breeding, and use of the strain, so as to solve the problem that wild *Ganoderma Lucidum* strains cannot meet requirements of large-scale production of *Ganoderma* products.

In one aspect, the present application provides a *Ganoderma Lucidum* strain suitable for large-scale liquid fermentation, which is named as *Ganoderma Lucidum* G2, deposited with China General Microbiological Culture Collection Center under the accession number CGMCC No. 3982 on Jul. 20, 2010.

In one aspect, the present application provides a method of obtaining a *Ganoderma Lucidum* strain suitable for large-scale liquid fermentation by mutagenizing and breeding, the method comprising the steps of (1) subjecting pileus and stipe of non-lignified wild *Ganoderma* fruiting body to protoplast isolation, inoculating the isolate into a basic medium for culturing for 10~20 days, and subjecting the resultant *Ganoderma* mycelia to repeated isolation and purification, thereby obtaining wild-type naïve *Ganoderma* mycelia;

(2) inoculating the wild-type naïve *Ganoderma* mycelia from step (1) into a basic medium for culturing, then into a fermentation broth for culturing in a shaker, thereby obtaining a suspension of the wild-type naïve *Ganoderma* mycelia;

(3) subjecting the wild-type naïve *Ganoderma* mycelia from step (2) to a combinatory mutagenizing and breeding process of UV radiation, $NaN_3$ chemical mutagenesis and transient heating in sterile water at 80° C.~90° C., thereby obtaining a *Ganoderma* Lucidum strain suitable for efficient production of *Ganoderma* mycelia in large-scale liquid fermentation.

In one aspect, the present application provides use of a *Ganoderma Lucidum* strain suitable for large-scale liquid fermentation in manufacturing oral solution or beverage comprising *Ganoderma* mycelia or extracts of Ganoderma mycelia as main active ingredient.

In some embodiments, the oral solution or beverage may be a raw mycelia culture obtained from large-scale liquid fermentation of the *Ganoderma Lucidum* strain of the present application.

In some embodiments, the oral solution or beverage may be a *Ganoderma* oral solution or beverage with particular healthcare activity prepared by taking a raw mycelia culture obtained from large-scale liquid fermentation of the *Ganoderma Lucidum* strain of the present application as a main active ingredient with addition of adjuvants or excipients directed to the particular healthcare activity.

In some embodiments, the oral solution or beverage may contain extract of *Ganoderma* mycelia as a main active ingredient. The extract may be *Ganoderma* polysaccharide, *Ganoderma* organic germanium, *Ganoderma* terpenes. A *Ganoderma* oral solution or beverage with particular healthcare activity may be prepared by further adding adjuvants or excipients directed to the particular healthcare activity.

The *Ganoderma Lucidum* strain suitable for large-scale liquid fermentation of the present application is obtained by artificial mutagenizing and breeding, and is suitable for large-scale liquid fermentation. The *Ganoderma Lucidum* strain of the present application belongs to Ganodermataceae, genus *Ganoderma,* species *Ganoderma Lucidum* (W. curt. :Fr.)Karst.

The condition suitable for growth of mycelia comprises a temperature of 30° C.±1° C., pH of 4.5~5.5, culture duration of 10~12 days. The temperature suitable for growth of sporocarp is 25° C.~30° C., and its growth cycle is usually 1 to 3 years. Pileus is in semicircle, kidney or circle shape, and in woody texture. Pileus has a width of 5~15cm, and a thickness of 0.8~1 cm. Pileus is reddish-brown and has paint gloss. Pileus has ring ridges, radial wrinkles, and a thin edge usually introverted. The flesh is white or light brown. The tube face is initially white, and then becomes light brown, and then brown. Tubes have a density of 3~5/mm. Stalk grow by side or occasionally grow in a deflected direction. Stalk has a length of 3~15 cm, and a diameter of 1~3 cm. Stalk is purple-brown and has paint gloss. Spores are brown, and in an egg shape. Spores have sizes of 9~12 μm×4.5~7.5 μm. Sporocarp has a middle to large size and may be larger.

The production of mycelia using the *Ganoderma Lucidum* strain G2 of the present application is 80~120 times higher as compared with the production of mycelia using wild-type naïve *Ganoderma Lucidum* strain. The mycelia have contents of main pharmaceutical ingredients higher than those in wild-type naïve *Ganoderma Lucidum* strain, including (in wt/wt %) *Ganoderma* polysaccharide 16.8%. *Ganoderma* organic germanium 5.8%, terpenes with 28 or less C atoms 5.6%, small proteins (LZ-8) 16.6%, adenosine 3.6%, and mannitol 4.6%.

In practice, *Ganoderma* mycelia are obtained by a liquid fermentation with the following conditions:

the medium used for culturing the *Ganoderma Lucidum* strain G2 suitable for large-scale liquid fermentation of the present application has the following composition:

| | |
|---|---|
| $(NH_4)_2HPO_4$ | 0.8 g |
| $KH_2PO_4$ | 0.5 g |
| $MgSO_4\ 7H_2O$ | 0.05 g |
| NaCl | 1 g |
| $FeSO_4\ 7H_2O$ | 0.03 g |
| sucrose | 25 g |
| maltose | 5 g |
| peptone | 3 g |
| silkworm chrysalis meal | 2 g |
| extract of potato | 1000 ml; | wherein the extract of potato is prepared by cutting 300 g of potato into pieces, boiling the potato pieces in 1000 ml of purified water for 20 min followed by filtration;

and the fermentation condition comprises:

optimal culture temperature: 32±1° C.;

content of dissolved oxygen: 0.05 mmol/L~0.20 mmol/L;

pH: 4.5~5.5.

The large-scale culture lead to the yield of dry mycelia of about 6~8 g/1000 ml. Main pharmaceutical ingredients in mycelia include (in wt/wt %) *Ganoderma* polysaccharide 16.8%. *Ganoderma* organic germanium 5.8%, terpenes with 28 or less C atoms 5.6%, small proteins (LZ-8) 16.6%, adenosine 3.6%, and mannitol 4.6%.

The oral solution prepared using the *Ganoderma Lucidum* strain suitable for large-scale liquid fermentation of the present application is enriched in *Ganoderma* polysaccharide, *Ganoderma* organic germanium, triterpenes, and other active ingredients. The oral solution has a stable composition, and is advantageous in controlling blood pressure, reducing blood viscosity, cleansing blood, promoting cell activation, preventing arteriosclerosis, improving metabolism, enhancing immunity, improving sleep quality, improving male health, calming nerves, scavenging free radicals, treating and preventing cancers, and delaying aging.

According to the invention, pileus and stipe containing non-lignified *Ganoderma* sporocarp collected from nature are subjected to protoplast isolation to obtain *Ganoderma* mycelia which is then subjected to genetic breeding and mutagenizing to screen out a superior strain for large-scale production (*Ganoderma* mycelia as seed).

DETAILED DESCRIPTION OF EMBODIMENTS

The embodiments of the present application will be described with reference to the following examples. It should be understood that, the following examples are part, but not all, of the embodiments of the present application. Based on the following examples, a person skilled in the art would conceive of other variations without inventive effort, which are within the scope of the claims.

EXAMPLE 1

A *Ganoderma Lucidum* strain suitable for large-scale liquid fermentation, which is named as *Ganoderma Lucidum* G2, deposited with China General Microbiological Culture Collection Center under the accession number CGMCC No. 3982 on Jul. 20, 2010.

The *Ganoderma Lucidum* strain suitable for large-scale liquid fermentation of the present application is obtained by artificial mutagenizing and breeding, and is suitable for large-scale liquid fermentation. The *Ganoderma Lucidum* strain of the present application belongs to Ganodermataceae, genus *Ganoderma*, species *Ganoderma Lucidum* (W. curt.:Fr.)Karst.

The condition suitable for growth of mycelia comprises a temperature of 30° C.±1° C., pH of 4.5~5.5, culture duration of 10~12 days. The temperature suitable for growth of sporocarp is 25° C.~30° C., and its growth cycle is usually 1 to 3 years. Pileus is in semicircle, kidney or circle shape, and in woody texture. Pileus has a width of 5~15 cm, and a thickness of 0.8~1 cm. Pileus is reddish-brown and has paint gloss. Pileus has ringlike ridges, radial wrinkles, and a thin edge usually introverted. The flesh is white or light brown. The tube face is initially white, then becomes light brown, and then brown. Tubes have a density of 3~5/mm. Stalk grow by side and occasionally grow in a deflected direction. Stalk has a length of 3~15 cm, and a diameter of 1~3 cm. Stalk is purple-brown and has paint gloss. Spores are brown, and in an egg shape. Spores have sizes of 9~12 μm×4.5~7.5 μm. Sporocarp has a middle to large size and may be larger.

The production of mycelia using the *Ganoderma Lucidum* strain G2 of the present application is 80-120 times higher as compared with the production of mycelia using wild-type naïve *Ganoderma Lucidum* strain. The mycelia have contents of main pharmaceutical ingredients higher than those in wild-type naïve *Ganoderma Lucidum* strain, including (in wt/wt %) *Ganoderma* polysaccharide 16.8%, *Ganoderma* organic germanium 5.8%, terpenes with 28 or less C atoms 5.6%, small proteins (LZ-8) 16.6%, adenosine 3.6%, and mannitol 4.6%.

The medium used for culturing the *Ganoderma Lucidum* strain G2 suitable for large-scale liquid fermentation of the present application has the following composition:

| | |
|---|---|
| $(NH_4)_2HPO_4$ | 0.8 g |
| $KH_2PO_4$ | 0.5 g |
| $MgSO_4\ 7H_2O$ | 0.05 g |
| NaCl | 1 g |
| $FeSO_4\ 7H_2O$ | 0.03 g |
| sucrose | 25 g |
| maltose | 5 g |
| peptone | 3 g |
| silkworm chrysalis meal | 2 g |
| extract of potato | 1000 ml; | wherein the extract of potato is prepared by cutting 300 g of potato into pieces, boiling the potato pieces in 1000 ml of purified water for 20 min followed by filtration;

and the fermentation condition includes:

optimal culture temperature: 32±1° C.;

content of dissolved oxygen: 0.05 mmol/L~0.20 mmol/L;

pH: 4.5~5.5.

The large-scale culture leads to the yield of dry mycelia of about 6~8 g/1000 ml. Main pharmaceutical ingredients in mycelia include(in wt/wt %) *Ganoderma* polysaccharide 16.8%, *Ganoderma* organic germanium 5.8%, terpenes with 28 or less C atoms 5.6%, small proteins (LZ-8) 16.6%, adenosine 3.6%, and mannitol 4.6%. The production of mycelia is 80-120 times higher as compared with the production of mycelia using wild-type naïve *Ganoderma Lucidum* strain.

EXAMPLE 2

The method of obtaining a *Ganoderma Lucidum* strain suitable for large-scale liquid fermentation by mutagenizing and breeding comprises the following steps.

Step 1: Subjecting pileus and stipe of non-lignified wild *Ganoderma* fruiting body collected from *Prunus mume* Apricot to protoplast isolation, inoculating the isolate thus obtained into a basic medium for culturing at a temperature of 28° C.~30° C. for 15 days, and subjecting the resultant *Ganoderma* mycelia to repeated isolation and purification, thereby obtaining wild-type naïve *Ganoderma* mycelia;

wherein the basic medium used in protoplast isolation and purification carried out on pileus and stipe of non-lignified wild *Ganoderma* fruiting body has the following composition:

| | |
|---|---|
| $(NH_4)_2HPO_4$ | 0.3 g |
| $KH_2PO_4$ | 0.2 g |
| $MgSO_4 \cdot 7H_2O$ | 0.02 g |
| NaCl | 0.5 g |
| $FeSO_4 \cdot 7H_2O$ | 0.03 g |
| sucrose | 20 g |
| sterile water | 1000 ml. |

Step 2: Inoculating the wild-type naïve *Ganoderma* mycelia from Step 1 into a basic medium for culturing, then into a fermentation broth for culturing in a shaker, thereby obtaining a suspension of the wild-type naïve *Ganoderma* mycelia;

wherein (1) the components and their contents of the basic medium was optimized by a single factor orthogonal experiment, in order to obtain a medium suitable for the growth of wild-type naïve *Ganoderma*.

The orthogonal experiment was carried out as follows.

5000 ml of purified water was divided into 25 flasks with 200 ml for each. The flasks were numbered 1~25, and divided into five groups, i.e., Nos. 1~5, Nos. 6~10, Nos. 11~15, Nos. 16~20, and Nos. 21~25. Basic medium with different composition was added into the flasks respectively, as shown in table 1.

TABLE 1

(unit: g)

| | basic medium Nos. | | | | |
|---|---|---|---|---|---|
| | 1~5 | 6~10 | 11~15 | 16~20 | 21~25 |
| $(NH_4)_2HPO_4$ | 0.3 | 0.6 | 0.5 | 0.3 | 0.8 |
| $KH_2PO_4$ | 0.5 | 0.5 | 0.2 | 0.5 | 0.3 |
| $MgSO_4 \cdot 7H_2O$ | 0.02 | 0.05 | 0.04 | 0.04 | 0.05 |
| NaCl | 0.5 | 0.5 | 0.8 | 0.5 | 0.5 |
| $FeSO_4 \cdot 7H_2O$ | 0.03 | 0.03 | 0.03 | 0.03 | 0.03 |
| sucrose | 20 | 30 | 20 | 30 | 20 |
| peptone | 3 | 3 | 2 | 3 | 2 |

The medium was subjected to high pressure sterilization and then used for culturing the naïve *Ganoderma* mycelia for 12 days. Then, the mycelia in flasks No. 1~25 were filtered, and dried at a temperature of 105±1° C. for 24 h. Then, the dried mycelia were weighed, and the average weight of mycelia for each group was calculated and compared with each other. An optimal basic medium with following composition was established.

| | |
|---|---|
| $(NH_4)_2HPO_4$ | 0.6 g |
| $KH_2PO_4$ | 0.5 g |
| $MgSO_4 \cdot 7H_2O$ | 0.05 g |
| NaCl | 0.5 g |
| $FeSO_4 \cdot 7H_2O$ | 0.03 g |
| sucrose | 30 g |
| peptone | 3 g |
| sterile water | 1000 ml. |

(2) Based on the optimal basic medium established from the above single factor orthogonal experiment, a multiple factor orthogonal experiment was carried out by selecting different nitrogen sources, carbon sources, trace elements, culturing temperature and oxygen requirement as the factors. The optimal fermentation conditions finally established included the following.

The fermentation broth has the following composition:

| | |
|---|---|
| $(NH_4)_2HPO_4$ | 0.8 g |
| $KH_2PO_4$ | 0.5 g |
| $MgSO_4 \cdot 7H_2O$ | 0.05 g |
| NaCl | 1 g |
| $FeSO_4 \cdot 7H_2O$ | 0.03 g |
| sucrose | 25 g |
| maltose | 5 g |
| peptone | 3 g |
| silkworm chrysalis meal | 2 g |
| sterile water | 1000 ml; | and the fermentation condition includes:

optimal culture temperature: 32±1° C.;
content of dissolved oxygen: 0.05 mmol/L-0.20 mmol/L;
pH: 4.5~5.5.

Step 3: subjecting the wild-type naïve *Ganoderma* mycelia from Step 2 to a combinatory mutagenizing and breeding process which combines UV radiation, $NaN_3$ chemical mutagenesis and transient heating in sterile water at 80° C.~90° C., thereby obtaining a *Ganoderma Lucidum* strain suitable for efficient production of *Ganoderma* mycelia in large-scale liquid fermentation.

In Step 3, UV radiation is performed first. In particular, three samples of suspensions containing wild-type naïve *Ganoderma* mycelia (10 wt/wt %) were prepared, and named as Sample 1, Sample 2 and Sample 3. the wild-type naïve *Ganoderma* mycelia were irradiated with a 40 W UV lamp from a distance of 20 cm, and the radiation durations were set as below.

| | Sample No. | | |
|---|---|---|---|
| | 1 | 2 | 3 |
| radiation duration (min) | 5 | 10 | 20 |

Next, Sample 2 which is irradiated for 10 min had a lethality rate of 93% was selected in further experiments.

After culturing Sample 2, three samples of suspensions containing mycelia (10 wt/wt %) were prepared, and named Sample 4, Sample 5 and Sample 6. The samples were subjected to chemical mutagenesis with a chemical mutagenesis agent.

$NaN_3$ is selected as the chemical mutagenesis agent. In particular, 1 g of $NaN_3$ of 1.2 equivalent was dissolved into a mixture of 5 ml of dimethylformamide (DMF) and 5 ml of dimethyl sulfoxide (DMSO),thereby obtaining the chemical mutagenesis agent. Sample 4, Sample 5 and Sample 6 were added to the chemical mutagenesis agent for chemical mutagenesis treatment. The durations of chemical mutagenesis were set as follows.

|  | Sample Nos. | | |
| --- | --- | --- | --- |
|  | 4 | 5 | 6 |
| duration of chemical mutagenesis (min) | 5 | 10 | 20 |

Finally, transient heating in sterile water was carried out. In particular, Sample 4, Sample 5 and Sample 6 were washed with sterile water three times using centrifugation, and then subjected to transient heating in sterile water at 80° C.~90° C. The durations of transient heating were set as follows.

|  | Sample Nos. | | |
| --- | --- | --- | --- |
|  | 4 | 5 | 6 |
| duration of transient heating (sec) | 1 | 5 | 10 |

Sample 6 was subjected to transient heating for 10 sec with a lethality rate of 96%. The survived strain was the *Ganoderma Lucidum* G2 which is suitable for liquid fermentation and can lead to high production of *Ganoderma* mycelia. The strain was deposited with China General Microbiological Culture Collection Center under the accession number CGMCC No. 3982.

EXAMPLE 3

This example relates to a use of a *Ganoderma Lucidum* strain suitable for large-scale liquid fermentation in manufacturing oral solution or beverage comprising *Ganoderma* mycelia or extracts of *Ganoderma* mycelia as main active ingredient.

In Example 3, *Ganoderma* mycelia are obtained by large-scale liquid fermentation with the medium and conditions described in Example 1.

The *Ganoderma Lucidum* strain of the present application is subjected to large-scale liquid fermentation to yield *Ganoderma* mycelia. Then, the *Ganoderma* mycelia, as main active ingredient, are used to prepare *Ganoderma* oral solution. The *Ganoderma* oral solution is enriched in *Ganoderma* polysaccharide, *Ganoderma* organic germanium, triterpenes, and other active ingredients, and has a stable composition.

The oral solution or beverage may be a raw mycelia culture obtained from large-scale liquid fermentation of the *Ganoderma Lucidum* strain of the present application. The oral solution is advantageous in many aspects, e.g., immunity improvement, blood pressure control, lowering of blood viscosity, blood cleaning, cell activation promotion, arteriosclerosis prevention, metabolism improvement, sleep ameliorating, anti-allergy, male health improvement, nerves calming, and delaying aging.

The oral solution or beverage may also be a *Ganoderma* oral solution or beverage with particular healthcare activity prepared by supplementing a raw mycelia culture obtained from large-scale liquid fermentation of the *Ganoderma Lucidum* strain of the present application as the main active ingredient with adjuvants or excipients directed to the particular healthcare activity.

For example, polysaccharide extract of poria cocos, or polysaccharide extract of polyporus umbellatus may be added as medical adjuvants to prepare a *Ganoderma* oral solution especially beneficial to cancer patients. Vitamins or trace elements may be added as energy adjuvants to prepare a functional *Ganoderma* oral solution for improving physical ability.

We claim:

1. A method of obtaining a *Ganoderma lucidum* strain by mutagenizing and breeding, comprising the steps of
   (a) subjecting pileus and stipe of non-lignified wild *Ganoderma* fruiting body to protoplast isolation, inoculating the isolate into a basic medium for culturing for 10~20 days, and subjecting the resultant *Ganoderma* mycelia to repeated isolation and purification, thereby obtaining wild-type naïve *Ganoderma* mycelia;
   (b) inoculating the wild-type naïve *Ganoderma* mycelia from step (1) into a basic medium for culturing, then into a fermentation broth for culturing in a shaker, thereby obtaining a suspension of the wild-type naïve *Ganoderma* mycelia; and
   (c) subjecting the wild-type naïve *Ganoderma* mycelia from step (2) to a combinatory mutagenizing and breeding process of UV radiation, $NaN_3$ chemical mutagenesis and transient heating in sterile water at 80° C.~90° C., thereby obtaining a *Ganoderma lucidum* strain suitable for efficient production of *Ganoderma* mycelia in large-scale liquid fermentation.

2. The method of claim 1, wherein the basic medium used in step (a) for the protoplast isolation and purification of pileus and stipe of non-lignified wild *Ganoderma* fruiting body has the following composition:

| $(NH_4)_2HPO_4$ | 0.3 g |
| --- | --- |
| $KH_2PO_4$ | 0.2 g |
| $MgSO_4 \cdot 7H_2O$ | 0.02 g |
| NaCl | 0.5 g |
| $FeSO_4 \cdot 7H_2O$ | 0.03 g |
| sucrose | 20 g |
| sterile water | 1000 ml. |

3. The method of claim 1, wherein the basic medium in step (b) has the following composition:

| $(NH_4)_2HPO_4$ | 0.6 g |
| --- | --- |
| $KH_2PO_4$ | 0.5 g |
| $MgSO_4 \cdot 7H_2O$ | 0.05 g |
| NaCl | 0.5 g |
| $FeSO_4 \cdot 7H_2O$ | 0.03 g |
| sucrose | 30 g |
| peptone | 3 g |
| sterile water | 1000 ml. |

4. The method of claim 1, wherein the fermentation broth in step (b) has the following composition:

| $(NH_4)_2HPO_4$ | 0.8 g |
| --- | --- |
| $KH_2PO_4$ | 0.5 g |
| $MgSO_4 \cdot 7H_2O$ | 0.05 g |
| NaCl | 1 g |
| $FeSO_4 \cdot 7H_2O$ | 0.03 g |
| sucrose | 25 g |
| maltose | 5 g |
| peptone | 3 g |
| silkworm chrysalis meal | 2 g |
| sterile water | 1000 ml; | with the following fermentation condition:
optimal culture temperature: 32±1° C.,
content of dissolved oxygen: 0.05 mmol/L~0.20 mmol/L, and
pH: 4.5~5.5.

5. The method of claim 1, wherein the UV radiation in step (c) comprises irradiating the wild-type naïve *Ganoderma* mycelia with a 40 W UV lamp from a distance of 20 cm for 5-20 min;
the NaN$_3$ chemical mutagenesis comprises preparing a chemical mutagenesis agent by dissolving 1 g of NaN$_3$ of 1.2 equivalent into a mixture of 5 ml of dimethylformamide (DMF) and 5 ml of dimethyl sulfoxide (DMSO), and adding the wild-type naïve *Ganoderma* mycelia after UV radiation into the chemical mutagenesis agent for chemical mutagenesis treatment of 5-20min; and
the transient heating in sterile water comprises washing the wild-type naïve *Ganoderma* mycelia after chemical mutagenesis with sterile water, followed by transient heating in sterile water at 80° C.~90° C. for 1~10 sec.

6. The method of claim 5, wherein in step (c),
the radiation duration is 10 min in the UV radiation; and/or
the mutagenesis treatment duration is 20 min in NaN$_3$ chemical mutagenesis; and/or
in the transient heating in sterile water, sterile water at 85° C. is used and the heating duration is 10 sec.

7. The method of claim 1, wherein in step (a), the non-lignified wild *Ganoderma* fruiting body is collected from Prunus mume.

8. The method of claim 2, wherein in step (a), the non-lignified wild *Ganoderma* fruiting body is collected from Prunus mume.

9. The method of claim 3, wherein in step (a), the non-lignified wild *Ganoderma* fruiting body is collected from Prunus mume.

10. The method of claim 4, wherein in step (a), the non-lignified wild *Ganoderma* fruiting body is collected from Prunus mume.

11. The method of claim 5, wherein in step (a), the non-lignified wild *Ganoderma* fruiting body is collected from Prunus mume.

12. The method of claim 6, wherein in step (a), the non-lignified wild *Ganoderma* fruiting body is collected from Prunus mume.

* * * * *